United States Patent [19]
Meeker

[11] Patent Number: 6,127,118
[45] Date of Patent: *Oct. 3, 2000

[54] BCL-1 LOCUS NUCLEIC ACID PROBES AND ASSAY METHODS

[75] Inventor: Timothy C. Meeker, Lexington, Ky.

[73] Assignee: The Regents of the University of California, Oakland, Calif.

[*] Notice: This patent is subject to a terminal disclaimer.

[21] Appl. No.: 08/947,492

[22] Filed: Oct. 10, 1997

Related U.S. Application Data

[63] Continuation of application No. 08/472,893, Jun. 7, 1995, Pat. No. 5,677,130, which is a continuation of application No. 07/947,120, Dec. 17, 1992, Pat. No. 5,538,846.

[51] Int. Cl.[7] .............................. C12Q 1/68; C12P 19/34; C07H 21/04
[52] U.S. Cl. ..................... 435/6; 435/91.2; 536/23.1; 536/23.5; 536/24.31; 536/24.33
[58] Field of Search ................ 435/6, 91.2; 536/23.1, 536/23.5, 24.31, 24.33

[56] References Cited

PUBLICATIONS

Arnold et al. Journal of Clinical Investigation. 83: 2034–2040, 1989.
Arnold et al. Cold Spring Harbor Symposia on Quantitative Biology. 93–97, 1991.
Meeker et al. Blood. 74:1801–1806, 1989.
Meeker et al. Leukemia. 5:733–737, 1991.
Medeiros et al. Blood. 76:2086–2090, 1990.
Lee et al. Polymerase Chain Reaction. Cold Spring Harbor Laboratory Press, pp. 31–35, 1989.
Lammie et al. Oncogene. 6;439–444, 1991.
Motokura et al. Nature. 350:512–515, 1991.
Withers et al. Molecular and Cellular Biology. 11:4846–4853, 1991.
Rosenberg. Proceedings of the National Academy of Sciences, USA. 88: 9638–9642, 1991.
Korenberg. Trends in BioTechnology. 10:27–32, 1992.
Sambrook et al. Molecular Cloning: A Laboratory Manual. 7.37–7.77, Cold Spring Harbor Laboratory Press, N.Y., 1989.

*Primary Examiner*—Carla J. Myers
*Attorney, Agent, or Firm*—Townsend & Townsend & Crew, LLP

[57] ABSTRACT

Nucleic acid probes substantially complementary to nucleic acid sequences within the bcl-1 locus are disclosed as well as polymerase chain reaction (PCR) primers substantially complementary to nucleic acid sequences within that locus that are useful in detecting t(11;14)(q13;q32) translocations associated with hematopoietic cancers. Further, the bcl-1 locus probes are useful in detecting bcl-1 amplifications found in about twenty percent of solid tumors, particularly in squamous cell and mammary carcinomas. Diagnostic/prognostic methods for cancer are disclosed, as well as cancer research methods using the bcl-1 probes of this invention.

8 Claims, 8 Drawing Sheets

```
GTAGCAGGAGCAGAGAGTCCGCACGCTCCGGCGAGGGCAGAAGAGCGAGGGAGAGCCGAGCGCGG        90
ACCCAGCCAGGACCCCACAGCCCTCCCCAGCTGCCAGAGAGCCCATGAACACCAGCTCCTGTGCTGCTGAAGTGGAAACCATC  180
                                M  E  H  Q  L  L  C  C  E  V  E  T  I
CGCCGCGGCTACCCCGATGCCAACCTCCTCAACGACCGGGTGCTGCGGGCCATGCTGAAGGCCGAGGAGACCTGCGCCCCTGGTGTCC  270
 R  R  A  Y  P  D  A  N  L  L  N  D  R  V  L  R  A  M  L  K  A  E  E  T  C  A  P  S  V  S
TACTTCAAATGTGTGCAGAAGGAGGTCCTGCCGTCCATGCGGAAGATCGTGCCACCTGGATGCTGGAGGTCTGCGAGGAACAGAAGTGC  360
 Y  F  K  C  V  Q  K  E  V  L  P  S  M  R  K  I  V  A  T  W  M  L  E  V  C  E  E  Q  K  C
GAGGAGGAGGTCTTCCCGCTGGCCATGAACTACCTGGACCGCTTCCTGTCGCTGGAGCCCGTGAAAAAGAGCCGCCTGCAGCTGCTGGGG  450
 E  E  V  F  P  L  A  M  N  Y  L  D  R  F  L  S  L  E  P  V  K  K  S  R  L  Q  L  L  G
GCCACTTGCCATGTTCGTGCCCTCTAAGATGAAGGAGACCATCCCCCTGACGGCCGAGAAGCTGTGCATCTACACCGACAACTCCATCCGG  540
 A  T  C  M  F  V  A  S  K  M  K  E  T  I  P  L  T  A  E  K  L  C  I  Y  T  D  N  S  I  R
CCCGAGAGCTGCTGCAAATGGAGCTGCTCCTGGTGAACAAGCTCAAGTGGAACCTGGCCGCAATGACCCCACGATTCATTGAACAC  630
 P  E  E  L  L  Q  M  E  L  L  L  V  N  K  L  K  W  N  L  A  A  M  T  P  H  D  F  I  E  H
TTCCTCTCCAAAATGCCAGAAGGCGGAGAGAACAAACAGATCATCCGCAAACACGCGCAGACCTTCGTTGCCCTCTGTGCCACAGATGTG  720
 F  L  S  K  M  P  E  A  E  E  N  K  Q  I  I  R  K  H  A  Q  T  F  V  A  L  C  A  T  D  V
```

FIG. 2A

```
AAGTTCATTTCCAATCCGCCCTCCATGGTGGCAGCGTGTGGCCGAGCGTGCAAGCCCTGAACCTGAGGAGCCCCAACAACTTC  810
 K  F  I  S  N  P  P  S  M  V  A  A  G  S  V  V  A  A  V  Q  G  L  N  L  R  S  P  N  N  F

CTGTCCTACTACCGCCTCACACGCTTCCTCTCCAGAGTGATCAAGTGTGACCCGGACTGCTCCGGGCCTCCGAGGAGCAGATCGAAGCC  900
 L  S  Y  Y  R  L  T  R  F  L  S  R  V  I  K  C  D  P  P  D  C  L  R  A  C  Q  E  Q  I  E  A

CTGCTGGAGTCAAGCCTGCGCCAGGCCCAGCAGAACATGGACCCCAAGGCCGAGGAGGAGGAGGAGGAGGTGGACCTG  990
 L  L  E  S  S  L  R  Q  A  Q  Q  N  M  D  P  K  A  E  E  E  E  E  E  E  V  D  L

GCTTGCACACCACCGACGTGCGGGACGTGGACATCTGAGGGCGCCAGGCAGGCGGGGCCGCCACCCGCCGAGGGCCGAGCCGG  1080
 A  C  T  P  T  D  V  R  D  V  D  I  *

CCCCAGTGCTGCTCCACTGACAGTCCCTCCTCCGGAGCATTTGATACCAGAAGGGAAAGCTTCATTCCTCCTTGTTGTTGGTTGTTTTT  1170
CCTTGCTGCTCTTCCCCTTCCATCTCTGACTTAAGCACACTCTGAATCTCTTAAAGAGAGAGAGAAAAAAA  1260
AATAGTATTTGCATAACCCTGAGCCGTGGGGGAGGAGGTTGTGCTACAGATGATAGAGGCGCTCCGGAGGATTAGGTTCCATCGTTTT  1350
ATATTAATGTACTTGTTCTCTGTTGTAAGAATAGCATTAGAAAATTCAGCAAACCATTTTAAAGTAGAAGAGGGTTTAGTAGAAACATA  1440
TTAAAAAGCATAAAAACAATTTCCTGATAAAGCACACGTGTAGTGGGTTCTAGCCTGTAGTAGCTTGCTACTTGCTCATATGCATGTCACTTTATA  1530
AGTCATTGTATGTTATTATATTCCGTAGGTAGATGTGACCACCACCCAACAAACCATCAGTGACAAACCATCAGTGAGGTTGTCGGGCACC  1620
GCGTGGCCGTGTGCATGTCCTTTGCGCCTGTGACCACCACCCCAACAAACCATCAGTGACAAACCATCAGTGAGGTTGTCGGGCAC  1710
CAGCCAGCGTAGCAGGGTGCGGAAGGCCACCTGTCCCCACTCCTGCTCTAACGCTACGATACGCTACTATAAAGAGACGAAATAGTGACATAATATAT  1800
                                                                                          1890
```

FIG. 2B

```
TCTATTTTATACTCTTCCTATTTTTGTAGTGACCTGTTTATGAGATGCTGGTTTTCTACCCAACGGCCCTGCAGCCAGCTCACGTCCAG  1980
GTTCAACCCACAGCTACTTGGTTGTGTCTTCTCATATTCTAAAACCATTCCAAGCACTTCAGTCAGTCAGCACTTCAGTGCAAGAAA   2070
TAGCGCTGTTTTGTTGTGTGCAGGGAGGCAGTTTTCTAATGAATGGTTTGGGAATATCATGTACTTGTTGCAAGCAGGACTTT       2160
GAGGCAAGTGTGGGCCACTGTGTGTGGCAGTGGAGGTGTTTGGGAGGCTGCGTGCCAGTCAAGAAGAAAAAAGGTTGCATTCTCAC    2250
ATTGCCAGGATGATAAGTTCCTTTCCTTTCTTAAAGAAGTTGAAGTTTAGATGTTCACACCGAAGGTTTTAAACACTAAATATATAATT 2340
CTCAGAGGTTACCTAGAGAACAGTGGTTTTAAGGTGGTTTATCTTAGATGTTCAGAGGATGTTCATAAGGCCAGTATGATTTATAAATG 2430
TATAGTTAAGGCTAAAAGTATATTATTGCAGAGATGTTCATAAGGCCAGTATGATTTATAAATGCAATCTCCCCTGATTTAAACAC    2520
ACAGATACACACACACACACACAATCTCTGCCTTGATGTTACAGATTTAATACAGTTTATTTTTAAAGATAGATCCT             2610
TTTATAGGTGAGAAAAAAACAATCTGGAAGAAAAAAACACACCAAGTTCGGTTCCCAGAGTCATCTGATT                    2700
GGACAGGCATGGTGCAAGGAAATTAGGGTACTCAACCTAAGTTCGGTCTATTCTATCCCCTGCCCTTCCTTAAAAACT            2790
TAGTGACAAATAGACAATTTGCACATCTGGCTATATCCTGTAATTCTTGTAATTTTATTTAGGAAGTGTGAAGGAGGTGGCAAGAGTGTG 2880
GAGGCTGACGTGTGAGGGAGGACAGGCGCGGAGAGGAGGTCCCGAGGGGAAGGCGGTGCCACACCGGGACAGGCC               2970
GCAGCTCCATTTCTTATTGCCGCTGCTACCGTTGACTTCCAGGCACGGTTTGGAAATATTCACATCGCTTCGTATCTCTTTCACATT    3060
GTTTGCTGCTATTGGAGGATCAGTTTTTGTTTTACAATGTCATATACTGCCATGCTACTAGTTTTAGTTTTCTCTAGAACATTGTATTA  3150
CAGATGCCTTTTGTAGTTTGTTTTTTTTTTATGTGACCAGCGGTTCGCCTTGACCAGCCAGGTTCTGCGGGCAGGACACCGGGCGATCCAC 3240
TCACAATACCTCATGCTTCACTGGCCCCGGCCCCGAGGCGCTGGACCATGGTGGGCGTGCAGAACACGCGGGCGATCCCAC          3330
ACAGGCTGGCGGGCCACTTGATCTGGGGCACTTCATCTGATGCGCGAGGCGCTGTCCCAGAGACCAGCTGTGTTCCCCTTCTCTCCT    3420
GCGCCCTGTGATGCTGGGCCACTTCATCTGATCGGGGCGTAGCATCATAGTAGTTTTACAGCTGTGTTATTCTTTGCGTGTAGCTATGGA 3510
AGTTGCATAATTATTATTATTATTATAACAAGTGTCTTACTGCCACCACGGCGTTGTACCTGTAGGACTCTCATTCGGGATGAT      3600
TGGAATAGCTTCTGGAATTGTTCAAGTTTGGTATGTTTAATCTGTTATGTTCGTTTGTTATTGTTTGTAATTACAC              3690
CATAATGCTAATTTAAAGAGACTCCAAATCTCAATGAAGCCAGCTCACAGTGCTGTGCCCCGGTCATCTAGCAAGCTCCGAACCAAA    3780
AGAATTTGCACCCCGCTCGGGGCCCTCGGGTTGGGCCCTGCCAGGGCTCATCCTGCTCGGAGGCCATCTCGGCACAGGCCCC        3870
```

FIG. 2C

```
ACCCCGCCCCACCCCTCCAGAACACGGCTCACGCTTACCTCAACCATCCTGGCTCTGTCTGAACCACGCGGGGCCTTGAGGG   3960
ACGCTTGTCTGTCGTGATGGGCAAGGCACAAGTCCTGATGTTGTGTGTATCGAGAGGCCAAGGCTGGTGCAAGTGCACGGGGCA   4050
CAGCGGAGTCTGTCCTGTGACGCGCAAGTCTGAGGGTCTGGGCGGCTGCAATTTCTGCTGCACCGCGCGCTTCC   4140
CAGCACCACCAACATGTAACGGCATGTTTCCAGCAGAGAAGACAAACATGAAAGTCTAGAAATAAACTGGTAAAAC   4221
```

FIG. 2D

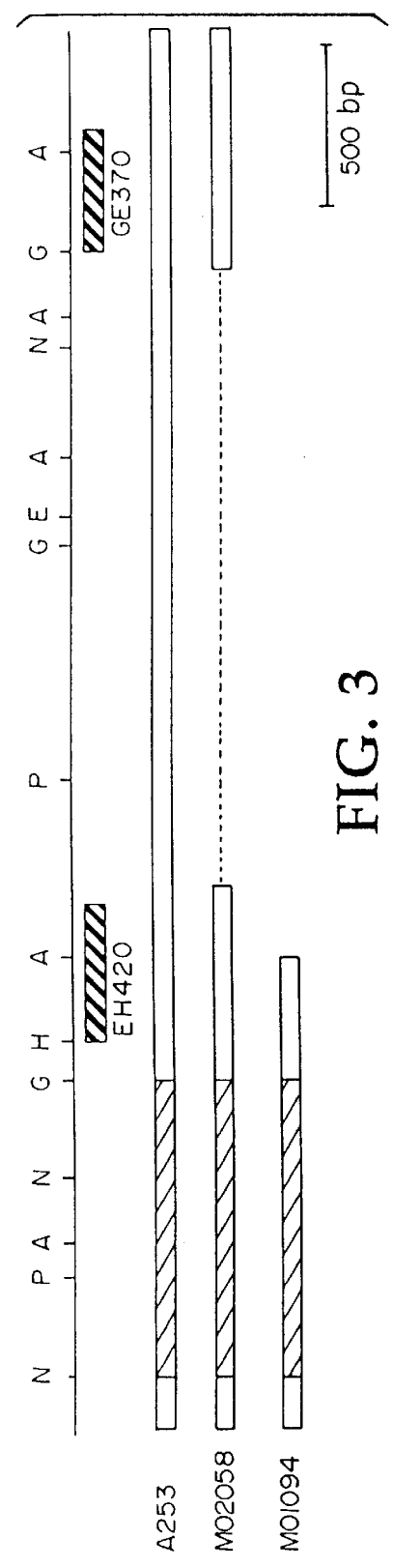

FIG. 3

```
         10         20         30         40         50         60
CTCGAGGCGG ACGGGGCCCC CTGCACCCCT CTTCCCTGGC GGGGAGAAAG GCTGCAGCGG
         70         80         90        100        110        120
GGCGATTTGC ATTTCTATGA AAACCGGACT ACAGGGGCAA CTCCGCCCGCA GGGCAGGCGC
        130        140        150        160        170        180
GGCGCCTCAG GGATGGCTTT TGGGCTCTGC CCTCGCTGCT CCCGGCGTTT GGCGCCCGCG
        190        200        210        220        230        240
CCCCCTCCCC CTGCGCCCGC CCCCGCCCCC CTCCCCGCTC CATTCTCTGC CGGGCTTTGA
        250        260        270        280        290        300
TCTTTGCTTA ACAACAGTAA CGTCACACGG ACTACAGGGG AGTTTTGTTG AAGTTGCAAA
        310        320        330        340        350        360
GTCCTGGAGC CTCCAGAGGG CTGTCGGCGC AGTAGCAGCG AGCAGCAGAG TCCGCACGCT
        370        380        390        400        410        420
CCGGCGAGGG GCAGAAGAGC GCGAGGGAGC GCGGGGCAGC AGAAGCGAGA GCCGAGGCGG
        430        440        450        460        470
GACCCAGCCA GGACCCACAG CCCTCCCCAG CTGCCCAGGA AGAGCCCCAG CCATGG
                                                        ‾‾‾‾‾‾
                                                        Nco I
```

FIG. 5

```
           10             20             30             40             50             60
AATTCTGGGG ACACAATTGG GCCCGTCACA CATGGGGTGG GCTCCAAGGG AAGTTGGTGC 70             80             90            100            110            120
AGTGGTCCTA GCTCTTGTGA CCGCATAAGC TCCAAAGGCT TGTTGGTATT CAGACCTGAG 130            140            150            160            170            180
GAATCAGAGG CCCAAGGAGG ACAGGAGACA CGGCTTTAGG TCCCCAGTTC TTTGTGGCAG 190            200            210            220            230            240
GACTGCCTCT CACCCAGGTC TCCACTCCCA GGAGACCTGT GGAAGGAGAA GACCCCTTCC 250            260            270            280            290            300
ACACTTGATG CCAGGCTTCT TATTACACAG ACCCTACTGC CTCAAAGGCC TCAAGTGACC 310            320            330            340            350            360
CCGGACTCAC TCACGCCCTG CAAGCAGGGG AACTGTCAGC ATCTGGCTAG GGCCATGTCA 370            380            390            400            410            420
GCTGCGATGG GCTGGGGCGA GCTACAGTAA GAGTGGGGCC CGTGGAGTGG GTTCCTGGGG 430            440            450            460            470            480
GAGCCCATCG TATGTCTAGC AGTTGCGGGC TTTTTGGGAT GTCAACCACC TCTGCTGGGA 490            500            510            520            530            540
AGGTGCTGGG CGTGGGTGGG TGGGTAAGAT GCTGGCTGAG TCATCTGTGT CCCCGAAATA 550            560
GGCTGTGGAA TGGGGAAGCT
```

FIG. 6

BCL-1 LOCUS NUCLEIC ACID PROBES AND ASSAY METHODS

This application is continuation of application Ser. No. 08/472,893 filed June. 7, 1995, now U.S. Pat. No. 5,677,130, which is a continuation of application Ser. No. 07/947,120, Sep. 17, 1992 now U.S. Pat. No. 5,538,846.

FIELD OF THE INVENTION

The present invention is in the general area of medical genetics and oncology. More specifically, it relates to the identification and characterization of a new gene—the bcl-1 gene—as well as nucleic acid probes and assay methods to identify translocations within the bcl-1 locus and amplifications of that gene. Such assay methods provide for improved diagnosis/prognosis of cancers associated with said translocations and amplifications. Further, said probes are useful in cell cycle progression studies.

This invention was made with Government support under Grant No. CA01102, awarded by the National Institutes of Health. The Government has certain rights in this invention.

BACKGROUND OF THE INVENTION

Chromosome translocations have been associated with many types of human leukemia and lymphoma. It is accepted that these translocations disrupt proto-oncogenes that are involved in the pathogenesis of these malignancies [Bishop, J. M., *Cell*, 64: 235 (1991); and Klein and Klein, *Nature*, 315: 190 (1985)]. The analysis of chromosome translocations in leukemia and lymphoma has led to the improved understanding of known oncogenes, such as c-myc and c-abl, and the discovery of new oncogenes, such as bcl-2 [Bakhshi et al., *Cell*, 41: 899 (1985); Cleary et al., *Cell*, 47: 19 (1986); Leder et al., *Science*, 222: 765 (1983); Showe and Croce, *Annu. Rev. Immunol.*, 5: 253 (1987); Swenson et al., *Cell*, 47: 861 (1986)].

The t(11;14)(q13;q32) translocation is an important abnormality associated with B-lymphocytic malignancy [Fukuhara et al., *Cancer Res.*, 39: 3119 (1979); Nishida et al., *Cancer Res.*, 49: 1275 (1989); Van den Berghe et al., *Cancer.* 44: 188 (1979); and Weisenburger et al., *Blood*. 69: 1617 (1987)]. That abnormality has been reported in chronic lymphocytic leukemia (CLL), multiple myeloma, and lymphoma [Yunis, J., *Science*, 221: 227 (1983); Van den Berghe et al., supra; Fukuhara et al., supra; Abe et al., *Cancer*, 61: 483 (1988); Chaganti et al., *Cytogenet. Cell Genet.*, 45: 93 (1987); and Barlogie et al., *Acta Hematol.*, 78: 171 (Suppl.; 1987)]. Breakpoints in chromosomal region 14q32 occur in the joining region of the immunoglobulin heavy chain (IgH) gene [Meeker et al., *Blood*, 74: 1801 (1989); Tsujimoto et al., *Nature* (London), 315: 340 (1986); and Tsujimoto et al., *Science*, 224: 1403 (1984)]. Chromosome 11 breakpoints occur in a region called the bcl-1 (B-cell lymphoma/leukeeia 1) locus, that was known to cover at least 63 kb of chromosome 11 [Koduru et al., *Oncogene*, 4: 929 (1989); Meeker et al. (1989), supra; Rabbitts et al., *Oncogene*, 3: 99 (1988); and Tsujimoto et al. (1986), suipra]. A high proportion of the documented chromosome 11 breakpoints are found in a subregion of the locus called the major translocation cluster (MTC) [Meeker et al. (1989); Tsujimoto et al. (1986)].

By analogy to other translocations, a new gene, a putative dominant oncogene that was activated by the t(11;14)(q13;q32) translocation, has been postulated for the bcl-1 locus for many years. However, the identification of such a bcl-1 gene has been elusive, and it had not been well characterized.

In one approach to identify the bcl-1 gene, a number of candidate oncogenes from 11q13 were mapped by using the radiation hybrid technique [Richard et al., *Am. J. Hum. Genet.*, 49: 1189 (1991); and Meeker et al., *Blood*, 76: 239a (abst. suppl.; 1990)]. That study indicated whether any known genes mapped close to the bcl-1 locus. Potential bcl-1 candidate genes CD5, CD20, c-sea, and protein phosphatase la were eliminated by that analysis.

In parathyroid adenomas, a gene called PRAD1 was shown to be occasionally activated by a pericentric inversion of chromosome 11 [Motokura et al., *Nature* (London), 350: 512 (1991); and Rosenberg et al., *Oncogene*. 6: 449 (1991)]. Motokura et al. show in FIG. 2($a$) the nucleotide sequence and predicted amino acid sequence of PRAD1 cDNA. The PRAD1 gene is considered therein to be a bcl-1 -linked candidate oncogene.

Xiong et al., *Cell*, 65: 691 (1991), found the bcl-1 gene (called the cyclin D1 gene) in a screen for human genes that complement yeast cells deficient in $G_1$ cyclin activity.

Matsushime et al., *Cell*, 65: 701 (1991), found an apparent murine homolog of bcl-1 (called Cyl-1) by screening a mouse macrophage cell line for genes that might regulate $G_1$ progression in the presence of colony-stimulating factor 1.

Abnormalities of the bcl-1 locus are important in several subtypes of B-lymphocytic leukemia and lymphoma [Medeiros et al, *Blood*, 76: 2086 (1990); Rimokh et al., *Genes Chromosomes Cancer*, 2: 223 (1990); and Williams et al., *Blood*, 76: 1387 (1990)]. Further, the bcl-1 locus has been implicated in several other types of cancer. Amplifications of bcl-1 are detected in approximately 20% of breast cancer and squamous cell cancers [Ali et al., *Oncogene*, 4: 89 (1989); Berenson et al., *Oncogene*, 4: 1111 (1989); and Theillet et al., *Oncogene*, 5: 147 (1990)]. Data indicates that bcl-1 is expressed in human tumor cell lines representing those tumor types, and that there is an apparent correlation between amplification and expression in squamnous cell and mammary carcinomas [Lammie et al., *Oncogene*, 6: 493 (1991)].

Bcl-1 is known to be amplified without rearrangement in about a third of head and neck squamous cell carcinomas and a small number of squamous cell lung carcinomas, and is coamplified with hst and int-2 in a subset of human breast carcinomas [Berenson et al., *Oncogene*, 4: 1111 (1989); Berenson et al., *Oncogene*, 5: 1343 (1990); Ali et al., *Oncogene*, 4: 89 (1989); and Theillet et al., *Oncogene*, 5: 147 (1990)]. Further, bcl-1 is also amplified in bladder carcinomas [Proctor et al., *Oncogene*, 6: 789 (1991)]. Exploration of the pathophysiology of those diseases has awaited the identification and characterization of the bcl-1 gene.

Identified herein is a gene that is a member of the cyclin gene family whose expression is shown to be deregulated in two leukemia samples with the t(11;14)(q13;q32) translocation. That gene is considered to be the bcl-1 gene.

This invention characterizes the bcl-1 gene and provides nucleic acid probes to identify translocations and amplifications involving the bcl-1 locus that are associated with cancers. The structure of the bcl-1 gene and its relationship to translocations that occur within the bcl-1 locus are delineated by the instant invention. Further, the instant invention provides the first evidence that when t(11;14)(q13;q32) occurs that the bcl-1 gene is overexpressed as indicated by elevated levels of bcl-1 mRNA.

The nucleic acid probes of the instant invention are important for molecular diagnosis and/or prognosis of cancer and in cell cycle progression studies. Particularly, the bcl-1 probes provide an improved approach to diagnosing/ prognosing certain malignant lymphomas, a prolymphocytic variant of CLL, a proportion of multiple myelomas, and 20% of solid cancers, such as, breast and squamous cell cancers.

Prior to the instant invention, ten percent of human lymphomas were diagnosed by use of a light microscope only. Now, this invention provides the molecular tools to confirm such a diagnosis and allow for more exact clinical care. The probes of this invention could be used to analyse molecularly all human cancer specimens.

SUMMARY OF THE INVENTION

Disclosed herein is the cloning and analysis of about 140 kb of genomic DNA from the bcl-1 locus. Nucleic acid probes from that locus are described as are polymerase chain reaction (PCR) primers therefrom. Preferred nucleic acid probes of this invention comprise nucleic acid sequences that are substantially complementary to nucleic acid sequences within the bcl-1 locus on chromosome 11q13 wherein said probes comprise nucleic acid sequences that either are not substantially complementary to nucleic acid sequences within the bcl-1 gene exons, or are substantially complementary to nucleic acid sequences that encompass more of the bcl-1 locus then part or all of one or more exons from the bcl-1 gene.

The bcl-1 locus probes of this inventions are useful to detect t(11;14)(q13;q32) associated with certain hematopoietic cancers in conjunction with chromosome-specific painting (in situ hybridization), Southern blotting of DNA from human cancer samples, Northern blotting of RNA from such samples and RNase protection assays; as well as primers from the bcl-1 locus for PCR assays to detect that translocation. The human cells tested by such methods are human cells of myeloid or lymphoid origin. For example, cells from a lymph node biopsy, bone marrow cells such as stem cells or other blood cells can be tested for the t(11;14)(q13;q32) translocation by the methods of this invention.

For Northern blotting, it is necessary that the probes of this invention be substantially complementary to at least a portion of the bcl-1 coding region. The detection of bcl-1 mRNA from blood cells by Northern blotting is indicative of the presence of t(11;14)(q13;q32).

Southern blotting and chromosome-specific painting with the probes of this invention are preferred methods to detect t(11;14)(q13;q32). Chromosome-specific painting, more preferably FISH, with one or more of the bcl-1 locus probes of this invention is the most preferred method of detecting that translocation according to this invention.

Further, this invention provides for methods of using the bcl-1 locus probes of this invention to detect amplifications of the bcl-1 gene which occur in about 20% of solid tumors. Preferred methods of this invention to detect such amplifications include Southern and Northern blotting and chromosome-specific painting, preferably FISH, with the bcl-1 locus probes. More preferred are Southern blotting and chromosome-specific painting, preferably FISH, to detect such amplifications. Still more preferred is chromosome-specific staining, most preferably FISH, with the bcl-1 locus probes to detect such amplifications.

Using the assays of this invention, clinicians can correlate the phenototypic symptoms of a cancer with the information concerning whether the t(11;14)(q13;q32) translocation or bcl-1 amplification is present. Thereby, clinicians can quickly subclassify a cancer, for example, a lymphoma or breast cancer, as with or without t(11;14)(q13;q32) or a bcl-1 amplification, and make a diagnosis/prognosis based on that information. For example, the presence of a bcl-1 amplification in a breast carcinoma is considered to be a marker for poor prognosis [see Theillet et al., Oncogene, 5: 147–149 (1990) concerning coamplified oncogenes], and thus, if found, a more aggressive chemotherapeutic and/or radiation regimen could be selected as a treatment protocol.

Further, the probes of this invention can be used in cell cycle progression studies as a research tool, particularly as a cancer research tool.

BRIEF DESCRIPTION OF THE FIGURES

FIG. 2 provides the cDNA nucleotide sequence (4,221 bp) for bcl-1 derived from A253 cDNA clones (SEQ ID NO. 7). The 295-amino acid coding region is shown (SEQ ID NO. 8). The polyadenylation signal sequence is underlined. The nucleotide sequence data reported herein will appear in the EMBL, GenBank and DDBJ Nucleotide Sequence Databases under the accession number M73554.

FIG. 3 is a schematic comparing the three forms of the bcl-1 cDNA. The structure exhibited by the A253 cell line is the typical form of the bcl-1 mRNA in most human cell lines. The bcl-1 mRNA in M02058 results from the loss of 1,852 bp in the 3' untranslated region (dotted line). The bcl-1 mRNA in M01094 terminates as the result of a new polyadenylation signal sequence in the proximal 3' untranslated sequences. The open box represents the 5' untranslated sequences, the solid box the protein coding region and the stippled box the 3' untranslated sequences. Cross-hatched boxes represent probes derived from M02058 cDNA clones. Restriction sites are: A=AvaI; E=EcoRI; G=BqlI, H=HindIII; N=NcoI; and P=PstI.

FIG. 5 provides the sequence for a 476 nucleotide antisense genomic probe (SEQ ID NO. 9) that is from part of the area to which probe G13b hybridizes. That probe extends 5' from the NcoI site (location of translation initiation) shown in FIG. 3. This probe is used in RNase protection assays described herein.

FIG. 6 provides the sequence for the p11EH probe (560 bp) (SEQ ID NO. 10) which was used for chromosome walking to obtain the probes of this invention from readily accessible or commercially available genomic libraries.

NUCLEOTIDE AND AMINO ACID SEQUENCE SYMBOLS

Figure 1:
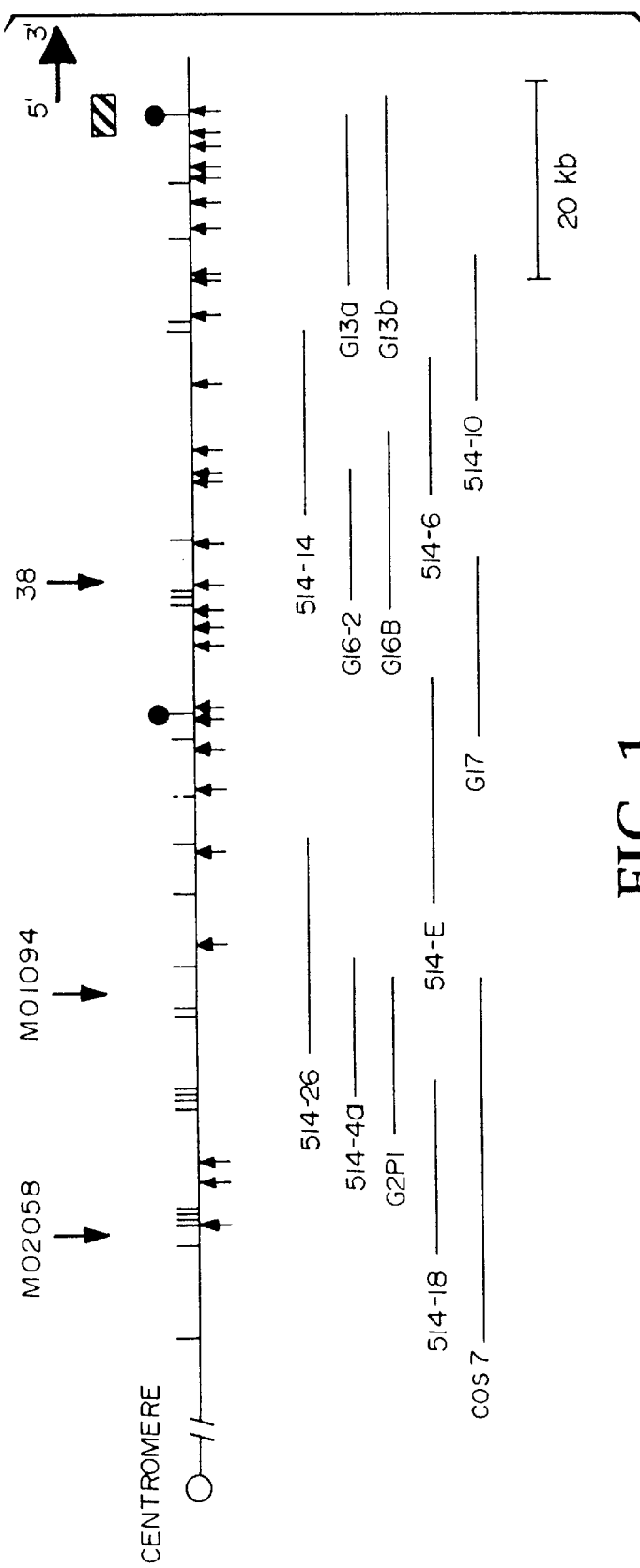
FIG. 1 is a diagram schematically representing more than 120 kb of the bcl-1 locus at human chromosome 11q13. The B4.0 genomic fragment (cross-hatched box) spans an HTF island and identifies the bcl-1 mRNA. The 5' end of the bcl-1 mRNA originates within the B4.0 probe, and transcription proceeds toward the telomere (as shown by the stippled arrow). The translocation breakpoint in the M02058 cell line occurred within the major translocation cluster, approximately 110 kb from the B4.0 probe. The M01094 and CLL 38 breakpoints are located approximately 85 and 47 kb from the B4.0 probe. All known HindIII (vertical lines) and EcoRI (arrows) restriction sites are indicated, as well as two hypomethylated EagI sites (solid circles). The locations of 13 normal phage clones and one cosmid clone are indicated.

The following symbols are used to represent nucleotides in the figures herein:

| Base | Symbol |
|---|---|
| adenine | A |
| cytosine | C |
| guanine | G |
| thymine | T |
| uracil | U |

It is further understood that the nucleotide sequences herein described represent only the precise structure of the nucleotide sequences isolated according to this invention. It is expected that slightly modified nucleotide sequences will be found or can be modified by techniques known in the art. DNA having equivalent codons is considered within the scope of the invention, as are synthetic DNA sequences, as well as those sequences but for the degeneracy of the genetic code would hybridize to the nucleotide sequences herein shown.

There are twenty main amino acids, each of which is specified by a different arrangement of three adjacent DNA nucleotides (triplet code or codon), and which are linked together in a specific order to form a characteristic protein. A one-letter convention is used herein to identify said amino acids, as, for example, in FIG. 2, as follows:

| Amino acid name | One-Letter Abbreviation |
|---|---|
| Alanine | A |
| Arginine | R |
| Asparagine | N |
| Aspartic Acid | D |
| Cysteine | C |
| Glutamic Acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

Abbreviations

The following abbreviations are used herein.

| | |
|---|---|
| A - | AvaI |
| ATCC - | American Type Culture Collection |
| B - | |
| bcl-1 - | B-cell leukemia/lymphoma-1 |
| bp - | base pair(s) |
| CLL - | chronic lymphocytic leukemia |
| DMSO - | dimethyl sulfoxide |
| dNTP - | deoxynucleotide triphosphate |
| E - | EcoRI |
| EDTA - | ethylenediaminetetraacetic acid |
| FIGE - | field inversion gel electrophoresis |
| FISH - | fluorescent in situ hybridization |
| G - | BalI |
| H - | HindIII |
| HTF - | HpaII-tiny fragment |
| kb - | kilobase |
| M - | molar |
| min - | minute |
| ml - | milliliter |
| mM - | millimolar |
| MTC - | major translocation cluster |
| N - | NcoI |
| ORF - | open reading frame |
| P - | PstI |
| PCR - | polymerase chain reaction |
| PIPES - | piperazine-N,N'-bis[2-ethane]-sulfonic acid |
| SSC - | 0.15 M NaCl/0.015 M Na citrate, pH7 |
| SDS - | sodium dodecyl sulfate |
| Sm - | SmaI |
| Ss - | SstI |
| µg - | micrograms |
| µl - | microliters |

| Cell Lines | |
|---|---|
| GM607 - | B lymphoblastoid cell line obtained from the Human Genetic Mutant Cell Repository [Camden, NJ (USA)] |
| MO - | the four cell lines with that prefix were derived from a culture of peripheral blood leukemic cells in the presence of Epstein-Barr virus as described in Meeker et al., Leukemia, 5(9): 733 (1991) M02058 and M01094 were derived from patients with chronic lymphocytic leukemia (CLL; prolymphocytic variant); both have the t(11;14)(q13;q32) translocation. The translocations in both those cell lines have been structurally characterized as described in Meeker et al., id. The M02058 cell line was derived from a male patient with a predominant karyotype of 461XY1-17, −20,t(11;14) (q13;q32), +der(17)t(1;17) (q32q44;p11), +der20t(1;20) (q25q32;q13) The M01094 cell line was developed from a female patient; the karyotype of all mitoses examined was 46,XX, t(11;14)q13;q32). M01079 and M01129 were also derived from CLL cells; however, the karyotype of those cell lines exhibited a trisomy of chromosome 12 without any evidence of any chromosome 11 abnormalities. Those cell lines were used as negative controls. |
| A253 - | squamous cell carcinoma cell line; obtained from the American, Type Culture Collection (ATCC; Rockvill, MD (USA)) |
| Tera-2 - | teratocarcinoma cell line; obtained from the ATCC |
| A431 - | cervical carcinoma cell line; obtained from the ATCC |
| FaDu - | esophageal carcinoma cell line; obtained from the ATCC |

-continued

| Cell Lines | |
|---|---|
| K562 - | erythroleukemia cell line; obtained from the ATCC |
| U-937 - | monocytic cell line; obtained from the ATCC |
| Reh - | B-lineage leukemia cell line; obtained from the ATCC; and |

All the cell lines were cultured at 37° C. in 5% $CO_2$ using the recommended media.

DETAILED DESCRIPTION

Identification and Characterization of Bcl-1 Gene

The strategy herein used for finding the bcl-1 gene was based on the hypothesis that the bcl-1 gene would be associated with the first HpaII-tiny-fragment (HTF) island telomeric of the bcl-1 locus breakponts described in Meeker et al., *Blood,* 74: 1801 (1989) and Meeker et al., *Leukemia.* 5(9): 733 (1991). That model was based on previous findings that 1) in translocations involving the IgH locus, the activated oncogene is found upstream of the IgH enhancer, and 2) genes are frequently associated with HTF islands [Lindsay and Bird, *Nature* (London), 327: 336–338 (1987)]. The technique of chromosome walking was used to isolate normal genomic clones extending telomeric on chromosome 11 from the sites of the translocations to the first HTF island (FIG. 1).

Early in the search, methylation-sensitive restriction enzymes and field inversion gel electrophoresis (FIGE) were used to estimate the distance to the first telomeric HTF island. An EagI restriction site, 55 kb telomeric of the breakpoint in the M02058 cell line, was identified that could be digested in genomic DNA from normal human granulocytes and the GM607 lymphoblastoid cell line (FIG. 1). That EagI site was not in an HTF island. Using that restriction site as a landmark, the distance to the next telomeric, hypomethylated EagI site was determined to be 50–60 kb (FIG. 1). In addition, no cutting by BssHII, SacII or NotI between those two EagI sites could be documented. It was concluded that there might be an HTF island approximately 110 kb telomeric of the MTC.

As hypothesized, the first HTF island was located 110 kb telomeric of the MTC and 47 kb telomeric of the breakpoint from chronic lymphocytic leukemia (CLL) sample 38 (the most telomeric of the reported translocation breakpoints) [Meeker et al., (1989), supra]. That region is covered by the subcloned B4.0 probe shown in FIG. 1. In a 1.7 kb fragment of that probe, there were two SacII sites, one BssHII site, and a superimposed NotI and EagI site. Southern blotting using the B4.0 probe evidenced that the EagI site was hypomethylated and therefore, corresponded to the EagI site predicted in the FIGE experiments.

To determine whether a gene was associated with the HTF island, a Northern blot was performed using the B4.0 probe as described in Example 1. Four cell lines were studied, all derived from patients with CLL. In cell lines having the t(11;14)(q13;q32) translocation, a distinct transcript was identified. No transcript was evident in the two CLL cell lines without the translocation. The presence of a transcript only in the CLL lines containing the translocation indicated that the bcl-1 gene had been identified.

To determine the typical size of the bcl-1 mRNA, a large number of human cell lines were screened by Northern blotting. Most of the human cell lines expressed a 4.4 kb mRNA (accounting for 80–90% of the transcripts) with minor bands at 4.2 kb and 1.5 kb. One representative cell line, A253 (derived from a squamous cell carcinoma), was chosen for detailed study.

cDNA Sequences and mRNA from Cell Lines

To further characterize the bcl-1 gene, cDNA libraries were made from A253, M02058 and M01094. Representative cDNA clones from all three cell lines were sequenced and analyzed. The sequence derived from the A253 clones covers 4221 base pairs and contains a consensus polyadenylation signal sequence at the 3' end (FIG. 2). The sequence of the M02058 clones spans 2415 base pairs and is identical to that of A253 with the following exceptions (positions refer to numbering in FIG. 2): 1) 45 additional base pairs (co-linear with genomic DNA) are present at the 5' end; 2) a C is present at nucleotide 281 instead of G, resulting in a change from cysteine to serine at amino acid 47; 3) a deletion occurred from nucleotides 1652 to 3503 (1852 bases in length); 4) a C is present at nucleotide 3759 instead of T; and 5) an additional C is present at the 3' end. The sequence of the M01094 clones covers 1353 base pairs and is identical to the A253 sequence except: 1) 6 additional base pairs are present at the 5' end; 2) nucleotide 68 is T instead of G; 3) nucleotide 271 is G instead of T (substituting an aspartic acid for tyrosine at amino acid 44); 4) nucleotide 864 is A instead of G; and 5) a consensus polyadenylation signal starting at nucleotide 1333 is generated by a 3 base pair deletion (AATAATCAACTC to AATAAACTC) (SEQ ID NO: 1).

The bcl-1 mRNAs from A253, M02058 and M01094 are compared schematically in FIG. 3. All three have the bcl-1 open reading frame (ORF) in common. The ORF starts at a methionine codon in a favored context for translation initiation [Kozak, M., *J. Mol. Biol.,* 196: 947–950 (1987)]. The ORF extends for 885 nucleotides and predicts a protein of 295 amino acids. All three forms of bcl-1 are different in the 3' untranslated region. A253 represents a typical transcript with a long 3' untranslated region. M02058 has undergone an internal loss of 1852 base pairs of the 3' untranslated region. Junctional sequences do not correspond to consensus splice signals [Senapathy et al., *Methods, Enzymol.,* 183: 252–278 (1990)]. In addition, a Southern blot of M02058 demonstrated that that loss resulted from a genomic deletion. M01094 is truncated in the proximal 3' untranslated region by the introduction of a new polyadenylation signal sequence.

The different sizes of bcl-1 mRNA in the three cell lines resulted from different 3' untranslated structures. In most cell lines that were studied (for example A253), the bcl-1 gene is expressed primarily as a 4.4 kb transcript. In contrast, the major 4.4 kb transcript was absent in both leukemia cell lines with the translocation. In the M02058 cell line, a 2.5 kb transcript was detected, and in the M01094 cell line, overexpression of a 1.5 kb transcript was found. In the three cell lines studied, the transcription start sites and protein coding regions were the same (except for an occasional point mutation). The transcript in M02058 resulted from the deletion of 1852 nucleotides in the 3' untranslated region, and the transcript in M01094 was truncated by the introduction of a new polyadenylation signal sequence. The data suggest that the loss of sequences in the 3' untranslated region of bcl-1 represents an additional aspect of activation, possibly by altering mRNA stability.

The relationship of the cDNA clones to the genomic map was determined. A selected region of approximately 500 bp from B4.0 was sequenced. It contained the 5' end of the cDNA clones from all three cell lines. From that data we determined that the 5' end of bcl-1 is centromeric, and that transcription proceeds toward the telomere (FIG. 1). That result was confirmed using Northern blotting with single stranded probes from the B4.0 region.

RNase Protection Assays

RNase protection assays were performed to determine the exact bcl-1 transcription start site within B4.0. An antisense genomic probe (FIG. 5) extending 5' from the NcoI site (location of translation initiation) was hybridized to RNA from several cell lines and subsequently digested with RNaseA and T1. In M02058, M01094, A253 and A431, a protected fragment of approximately 160 nucleotides was detected as described in Example 2. When considered with the fact that no isolated cDNA clone (of more than 20 analyzed) showed any evidence for the presence of an upstream exon, the experiment defined the primary start site for transcription. From the genomic map, it is clear that all t(11;14)(q13;q32) translocations described so far occur outside the transcribed region of the bcl-1 gene.

In Example 2 wherein a particular antisense genomic probe extending 5' from the NcoI site was used, the major protected fragment found was about 160 nucleotides, and minor protected fragments at about 172 and 195 bases were found. The detection of said protected fragments indicated that the translocation was present. If other genomic probes are used, different sized protected fragments would be indicative of the presence of t(11;14)(q13;q32).

Bcl-1 Sequences in Other Mammals

The bcl-1 gene was found to be highly conserved in evolution. Relatively stringent Southern blotting was performed and signals from mouse, rat, cow and pig were easily detected as described in Example 3. In work with the human Pim-1 gene under similar conditions, hybridization to mouse Pim-1 was not detected in spite of 89% overall nucleotide homology [Meeker et al., *Oncogene Res.*, 1: 87–101 (1987)]. Therefore, the human bcl-1 nucleotide sequence is anticipated to be very similar to that of mouse, rat, cow, and pig. DNA from Drosophila had a weak signal in our experiments whereas Xenopus and *S. cerevisiae* had no detectable signal.

Cyclin-Like

The deduced protein sequence from A253 was used to search the available data bases. The bcl-1 protein was found to have significant homology to several cyclins [Evans et al., *Cell.* 33: 389 (1983); Murray and Kirschner, *Nature (London)*, 339: 275 (1989); and Swenson et al., *Cell.* 47: 861 (1986)]. The highest similarity was found to A-type cyclins from human, African clawed frog (*Xenopus laevis*), Atlantic surf clam (*Spisula solidissima*) and fruit fly (*Drosophila melanogaster*) cells [Lehner and O'Farrell, *Cell*, 56: 957 (1989); Minshull et al., *EMBO J.*, 9: 2865 (1990); Pines and Hunter, *Nature (London)*, 346: 760 (1990); Swensen et al., *Cell*, 47: 861 (1986); Wang et al., *Nature (London)*, 343: 555 (1990); and Whitfield et al., *Nature (London)*, 338: 337 (1989)]. A comparison of the bcl-1 protein to those four A-type cyclins (110 amino acids including the cyclin box) support the inclusion of the bcl-1 in the cyclin family. Significant similarities to B-type cyclins were also detected.

However, the bcl-1 protein differs from other cyclins in two ways. First, bcl-1 is the smallest known member of the cyclin family, being significantly shorter at the amino terminus. Second, bcl-1 has nine consecutive glutamic acid residues close to the carboxy terminus.

As membership in the cyclin family might predict, it has been shown by others that bcl-1 mRNA and protein are expressed in relationship to cell cycle, and bcl-1 protein binds $p34^{cdc2}$ or closely related molecules [Matsushime et al., *Cell*, 65: 710 (1991); and Motokura et al., *Nature (London)*, 350: 512 (1991)]. As indicated below, bcl-1 may be selectively expressed in different tissues. Selective cyclin expression may represent one way in which different mammalian tissues adapt to specialized requirements for cell division.

Bcl-1 Expression

An extensive panel of human cell lines were surveyed for bcl-1 expression using Northern blotting of polyA+ RNA as described in Example 4. Whereas most human cell lines had easily detectable levels of bcl-1 mRNA, cell lines representing lineages derived from bone marrow stem cells (whether lymphoid or myeloid) exhibited no detectable levels of bcl-1 mRNA. Further, RNase protection assays of K562 exhibited no bcl-1 expression as described in Example 2. The only exceptions to the pattern were cell lines with the t(11;14) (q13;q32) translocation. All cell lines studied were rapidly growing in culture so that difference would not have resulted from the number of cells in cycle or the cell cycle kinetics in the cultures. The data indicated that bcl-1 is expressed at different levels in cell lines derived from different mammalian tissues.

The t(11;14)(q13;q32) translocation appears to activate bcl-1 by increasing levels of bcl-1 mRNA. All known translocation breakpoints fall outside the bcl-1 transcriptional unit. Therefore, there is no evidence for a fusion transcript or a fusion protein, as described for some other translocations. The elevated bcl-1 mRNA levels might result from an interaction between the immunoglobulin heavy chain (IgH) enhancer and the bcl-1 promotor, as described in some translocations involving the c-myc oncogene [Hayday et al., *Nature (Lond)*, 307: 334 (1984)]. That hypothesis would require activity of the IgH enhancer at distances up to 110 kb of genomic DNA, as suggested for some translocations that activate c-myc [Shtivelman and Bishop, *Mol. Cell Biol.*, 10: 1835 (1990)]. However, it is also possible that the translocation may eliminate a distant negative control element, leading to bcl-1 activation.

Conclusion

Evidence that the gene identified and characterized herein is the bcl-1 gene is as follows. First, it is associated with the first HTF island telomeric of the known bcl-1 translocation breakpoints. Second, it is activated in cell lines with the t(11;14)(q13;q32) translocation. Third, as a member of the cyclin family, its perturbation might be expected to lead to altered cell cycle progression.

Bcl-1 Locus Probes

Figure 4:
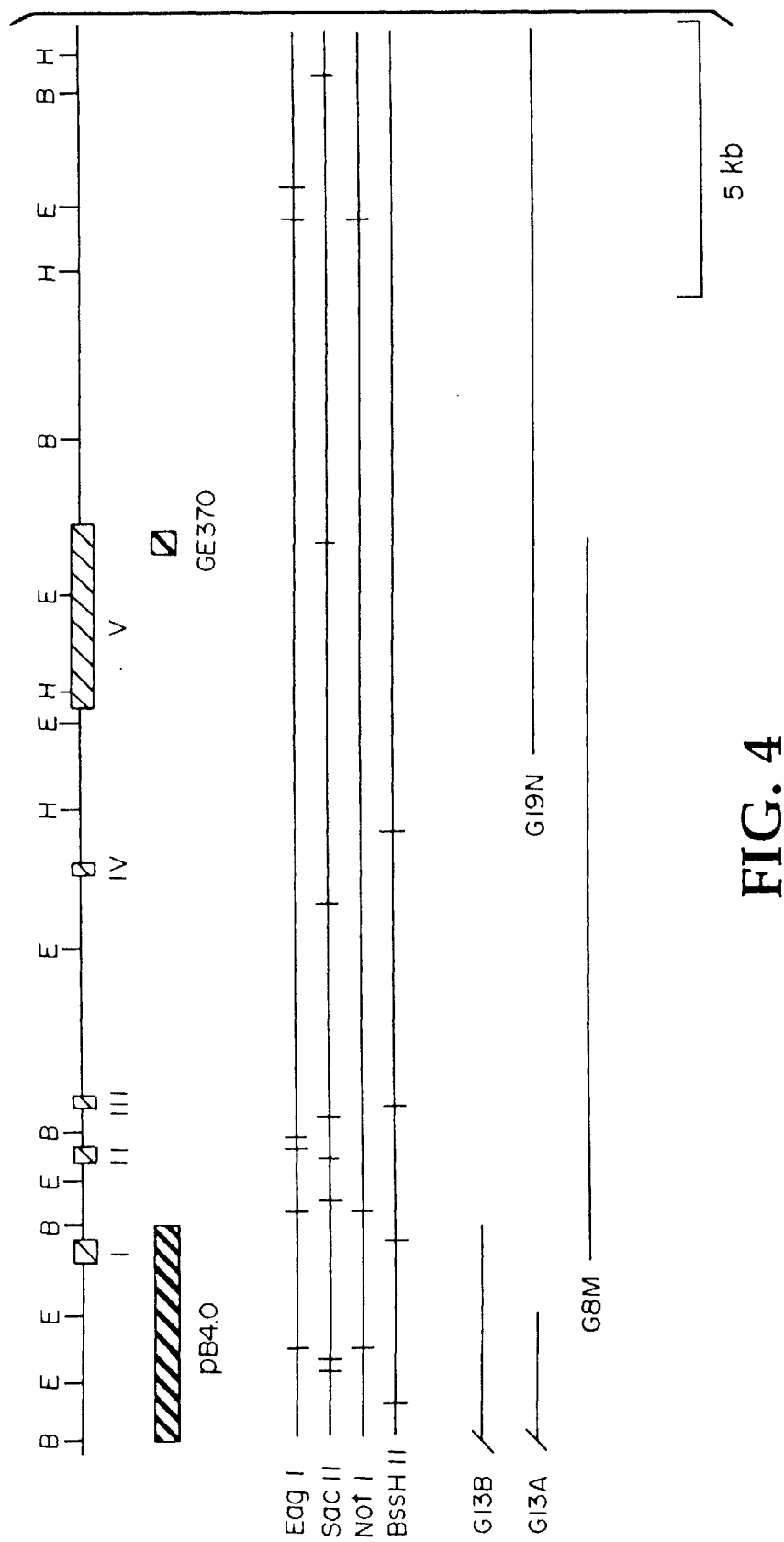
FIG. 4 is a diagram schematically representing about 27 kb of the bcl-1 locus at human chromosome 11q13. It is essentially a continuance (at a different scale) of FIG. 1 wherein the cross-hatched bbxes representing pB4.0 provide the point of overlap. The other cross-hatched box indicates the location of GE370, a probe at the 3' end of the fifth exon of the bcl-1 gene. Black solid boxes with Roman numerals I–V indicate the location of the exons of the bcl-1 gene within the bcl-1 locus. The 5' end of the gene and the centromere of chromosome 11 are to the left. Restriction sites for HindIII (H), EcoRI (E) and BamHI (B) are shown on the consensus map whereas sites for the EagI, SacII, NotI and BssHII restriction enzymes are indicated below. An HTF island covers the 5' end of the gene. The presence at the 3' end of one NotI site, two EagI sites (one of which coincides with the NotI site) and a close SacII site indicates a possible 3' HTF island.

Exemplary nucleic acid probes according to this invention are those shown in FIGS. 1 and 4, and equivalent probes, that is, probes from the bcl-1 locus, preferably from the approximately 140 kb of overlapping genomic clones shown in FIGS. 1 and 4. Preferred probes of this invention are those from the bcl-1 locus that are outside the region of the bcl-1 gene itself, that is, outside of the region covered by the exons denoted by Roman numerals I–V in FIG. 4. Such preferred probes include probes that hybridize both to the exons of the bcl-1 gene and also to the introns (all or parts of the exons and introns), as for example, the probes G8M and G19N. Preferred probes outside the region of the bcl-1 gene include, but are not limited to: cos7; 514-18; G2P1; 514-4a; 514-26; 514-E; 514-14; 514-6; 514-10; and G13a. other probes included within this invention are pB4.0 and G13b. Those probes are representative, and any number of equivalent overlapping probes would be useful according to this invention.

The probes of this invention can be obtained by the use of the conventional methodology of chromosome walking

[Sambrook et al., *Molecular Cloning: A Laboratory Manual* (2d edition) (Cold Spring Harbor Laboratory Press; Cold Spring Harbor, N.Y. (1989)] wherein a segment of nonrepetitive nucleic acid, preferably DNA, is used as a probe to identify a series of overlapping clones from one or more human genomic DNA libraries, for example, Sau3A partial digest libraries of genomic DNA [Sambrook et al., id.]. Chromosome walking in a step by step fashion allows one to move from an initial clone to overlapping clones. An exemplary segment of nonrepetitive DNA useful for chromosome walking is the probe p11EH or fragments thereof [Meeker et al., *Blood,* 74 (5): 1801–1806 (Oct. 1989)], the nucleotide sequence for which is shown in FIG. 6. The p11EH (526 bp) is from a breakpoint region in the bcl-1 locus located in the area indicated by a large arrow above which is the number 38 in FIG. 1.

A probe derived from the sequence for p11EH (FIG. 6) can be synthesized on an oligonucleotide synthesizer [for example, an Applied Biosystems (Foster City, Calif.) DNA synthesizer]. Alternatively, such a probe can be derived by PCR using two primers from the region and performing PCR on human genomic DNA. Such a probe derived from the p11EH sequence can be used to screen one or more human genomic DNA libaries to find overlapping clones equivalent to those shown in FIGS. 1 and 4.

It is preferred that the nucleic acid probes that are to be used for chromosome-specific painting be of high complexity, that is, contain in the order of about 35 kb or greater of nucleic acid sequences that are not repeated in the probe. The term "complexity" is defined herein according to the standard for nucleic acid complexity as established by Britten et al., *Methods of Enzymol.,* 29: 363 (1974) [see also Cantor and Schimmel, *Biophys. Chem.: Part III; The Behavior of Biological Macromolecules,* pp. 1228–1230 (Freeman and Co. 1986).].

Assays

Assays according to this invention are useful for diagnosing/prognosing hematopoietic cancers that are associated with the translocation t(11;14)(q13q32). Specifically, those hematopoietic cancers include subtypes of B-lymphocytic leukemia and lymphoma; more specifically those hematopoietic cancers include a relatively rare form of non-Hodgkin's B-cell lymphoma (5–10%) known as centrocytic lymphoma (closely related to intermediate lymphocytic lymphoma; also known as or mantle zone lymphoma), about 5–10% of multiple myelomas, about 10 to 20% of prolymphocytic leukemias and about 5 to 10% of chronic lymphocytic leukemias (CLLs), particularly prolymphocytic variants thereof.

To detect such translocations, preferred assays according to this invention are polymerase chain reaction (PCR) assays, preferably using the primers illustrated herein; and assays employing the nucleic acid probes of this invention in Northern blotting, in Southern blotting, in RNase protection assays, and in chromosome-specific painting.

Northern blotting to detect such translocations is particularly directed to detecting bcl-1 mRNA in cells derived from bone marrow stem cells (whether lympoid or myeloid). As indicated above and in Examples 1 and 4, cell lines representing lineages derived from bone marrow stem cells exhibited no detectable levels of bcl-1 mRNA except for those cell lines having t(11;14)(q13;q32). Thus, the presence of bcl-1 mRNA is cells of myeloid or lymphoid origin is indicative of the presence of t(11;14)(q13;q32).

For Northern blotting, it is necessary that the bcl-1 locus probes of this invention be substantially complementary to at least a portion of the coding region for bcl-1. Preferred probes to detect those mRNA transcripts by Northern blotting would be probes such as B4.0, G13b, G8M, G19N and/or probes equivalent thereto, wherein B4.0 and G13b are the more preferred probes.

Southern blotting and chromosome-specific staining, preferably fluorescent in situ hybridization (FISH), are preferred methods of detecting the t(11;14)(q13q32) translocation with the probes of this invention. Chromosome-specific painting, preferably FISH, is the most preferred method of detecting that translocation Preferred probes for detecting the t(11;14)(q13q32) translocation by chromosome-specific painting, preferably FISH, would be those of high complexity. An exemplary preferred combination of the probes would be a probe from the 5' end of the bcl-1 locus and one from the 3' end of the locus. For example, cos7 (FIG. 1), 514-18 or an equivalent probe from the 5' end of the locus and G13a, G13b, G8M or G19N (FIG. 4) from the 3' end, among many other possible probe combinations, would be useful in detecting the translocation by chrbmosome-specific painting.

A representative RNase protection assay of this invention to detect t(11;14)(q13;q32) is detailed below and in Example 4. Preferred probes of this invention for such an assay are those that extend 5' from the NcoI site (location of bcl-1 translation initiation as shown in FIG. 3). Particularly preferred is the antisense genomic probe of 476 bp shown in FIG. 5. When such a probe is employed, the detection of a protected fragment is a size range of approximately 160 nucleotides is indicative of the presence of a t(11;14) q13;q32) translocation.

Further, the assays of this invention are useful in providing improved diagnoses/prognoses of 20% of solid cancers. Amplifications of the bcl-1 gene are associated with a number of carcinomas including those of the urinary tract, particularly bladder cancers; gynecologic cancers, including cervical, ovarian, vaginal, endometrial and vulval cancers; brain tumors, such as gliomas and neuroblastomas; lung cancers; gastrointestinal cancers, including stomach and esophageal cancers, particularly esophageal cancers; adenocarcinomas, particularly breast tumors; and squamous cell carcinomas, particularly of the head and neck. Such assays to detect amplifications of the bcl-1 gene in solid tumors are most particularly directed to breast cancer and squamous cell carcinomas.

Preferred methods according to this invention of detecting such bcl-1 amplifications include the use of the probes of this invention in Northern blotting, in Southern blotting and in chromosome-specific painting. For Northern blotting, it is necessary that the bcl-1 probes be substantially complementary to at least a portion of the bcl-1 coding region. Preferred probes of this invention for use in Northern blotting to detect amplifications are B4.0, G13b, G8M, G19N and/or probes equivalent thereto.

The use of Southern blotting or chromosome-specific painting with the probes of this invention to detect bcl-1 amplifications are particularly preferred. The form of chromosome-specific painting known as FISH, wherein fluorescent labels are used to detect the probes that have hybridized to the target locus, is a particularly preferred method according to this invention.

Described herein are the assay methods based on chromosome-specific painting (preferably FISH), PCR, Southern and Northern blotting, and RNase protection assays that can be used to find the t(11;14)(q13;q32) translocations and/or the bcl-1 locus amplifications according to this invention.

Such assays provide valuable diagnostic/prognostic methods for evaluating neoplastic diseases. The assays of the invention are useful for screening a wide variety of neoplastic diseases, including both solid tumors and hematopoietic cancers. Knowledge of whether the t(11;14)(q13;q32) translocation or bcl-1 amplification is present in the cells of a patient may allow the attending physician to select the most appropriate therapy for that individual patient. For example, patients with a mammary carcinoma wherein bcl-1 amplification is present are apparently considered to require more aggressive therapy [see Theillet et al., *Oncogene* 5: 147–149 (1990)]. When bcl-1 amplification is not present, less vigorous therapies can be chosen. Because of severe patient distress caused by more aggressive therapy regimens, it is desirable to distinguish patients requiring such therapies.

Chromosome-Specific Painting

Chromosome-specific painting is a widely used methodology developed by Drs. Joe W. Gray and Daniel Pinkel at Lawrence Livermore National Laboratory in Livermore, Calif. (USA). It is described in Pinkel et al., *PNAS* (USA), 85: 9138–9142 (Dec. 1988), and in European Patent Application Publication No. 430,402 (published Jun. 5, 1991; EP 430,402) entitled "Methods and Compositions for Chromosome-Specific Staining". Other references concerning chromosome-specific painting include Patent Cooperation Treaty (PCT) International Publication No. 90/05789 (published May 31, 1990) entitled "In Situ Suppression Hybridization and Uses Therefor"; Cremer et al., *Hum. Genet.* 80: 235–246 (1988); Lichter et al., *Hum. Genet.,* 80: 224–234 (1988); and Lichter et al., *PNAS* (USA), 85: 9664–9668 (Dec. 1988).

In Section VIII of EP 430,402 (pages 37–40) and also in Tkachuk et al., *Science.* 250: 559–562 (Oct. 26, 1990) is described the use of chromosome-specific staining, specifically using fluorescent labels on the probes (thus, exemplary of FISH), to detect the reciprocal translocation t(9;22)(q34;q11) associated with chronic myelogenous leukemia (CML). Analogous chromosome-specific painting procedures can be used to detect the subject translocation of this invention—t(11;14)(q13;q32).

Further, chromosome-specific painting can be used to detect bcl-1 amplifications. When the bcl-1 locus is amplified, a proportionately larger (in extent) and/or brighter signal from the bcl-1 probes employed in chromosome-specific painting that hybridized to the target will be seen in comparison to the signal appearing in cells without a bcl-1 amplification.

PCR Assays

Primers from the areas of chromosome 11q13 can be used in polymerase chain reaction (PCR) assays to detect t(11;14)(q13;q32) translocations. Representative primers include the following:

| | |
|---|---|
| A. | 5'-GTCACCGTCTCCTCAGGT-3'(SEQ ID NO: 2) (18-mer derived from Jh sequences that are highly conserved in all 6 Jh regions on chromosome 14); |
| B. | 5'-GAGCTCCCTGAACACCTGGC-3'(SEQ ID NO: 3) (20-mer derived from normal sequence in the bcl-1 MTC region of chromosome 11); |
| C. | 5'-CTCATACGGTGTGTAGC-3'(SEQ ID NO: 4) (17-mer chromsome 11 primer); |
| D. | 5'-GGTTAGACTGTGATTAGC-3'(SEQ ID NO: 5) (18-mer chromosome 11 primer); and |
| E. | 5'-ACCTGAGGAGACGGTGAC-3'(SEQ ID NO: 7) (18-mer chromosome 14 primer). |

Preferred primers for chromosome 11 are primers (C) and (D), supra. A preferred chromosome 14 primer is (E). Of course, ones skilled in the art could select equivalent or many other primer combinations that would similarly detect t(11;14)(q13;q32). The PCR assay herein disclosed should detect between about 25% and about 50% of such translocations.

PCR is now a widely used molecular biology tool. It offers a rapid, sensitive and versatile cell-free molecular cloning system in which only minute amounts of starting material are required. PCR protocols, methods and applications are explained in Saiki et al., *Science,* 230 1350 (1985); U.S. Pat. Nos. 4,683,195 and 4,683,202 (both issued Jul. 28, 1987), 4,800,159 (issued Jan. 24, 1989) and 4,965,188 (issued Oct. 23, 1990); Erlich, H. A. (ed.), *PCR Technology: Principles and Applications for DNA Amplification* (W. H. Freeman and Company; NY; 1992); and Innis et al. (eds.), *PCR Protocols: A Guide to Methods and Applications* (Academic Press; San Diego, Calif.; 1990)].

A schematic outline of the PCR procedure involves the following steps: 1) obtaining a small cell sample to be tested; 2) isolating the DNA therefrom; 3) performing PCR with the selected primer combination; and 4) screening the PCR products for a band of the correct size. The presence of an amplified nucleic acid fragment of the correct size is a positive result indicating the presence of the translocation, whereas the absence of such a fragment is a negative result, indicating the absence of t(11;14) (q13;q32).

PCR can be used not only with fresh, frozen and viably maintained (as in DMSO) tissue or blood samples, but also with archived material, such as specimens that have been paraffin-embedded or formalin-fixed.

Materials and Methods

Delineated below are the particular materials and methods used as described herein to illustrate the invention. The cell lines used are described above after the Abbreviations.

Southern blots and aenomic libraries. Isolation of genomic DNA and Southern blotting were performed as previously described [Meeker et al. (1989), supra]. For Southern analysis, 10 µg of DNA was digested with the appropriate restriction endonuclease, electrophoresed in agarose gels, blotted on nylon membranes and washed as described in Meeker et al., id.

Hybridization to DNAs from heterologous species was performed in 30% formamide. Field inversion gel electrophoresis (FIGE) was performed using published methods [Carle et al., *Science,* 232: 65 (1986); and Gardiner et al., *Somatic Cell Mol. Genet.,* 12: 185 (1986)]. Unless otherwise stated, human genomic DNA was derived from peripheral blood granulocytes. Genomic DNA was also made from mouse liver, rat liver and pig peripheral blood buf fy coat. Cow genomic DNA was provided by Clontech [Palo Alto, Calif. (USA)]. *Xenopus laevis* DNA was a gift from J. Gautier [University of California at San Francisco (UCSF), San Francisco, Calif.] and *Saccharomvces cerevisiae* (strain SS13) [*S. cerevisiae*] DNA was a gift from the lab of I. Herskowitz (UCSF).

Genomic libraries were made as previously described [Frischauf et al., *J. Mol. Biol.,* 170: 827 (1983); Meeker et al. (1989), supra and Meeker et al., *J. Immunol.,* 141: 3994 (1988)]. Briefly, genomic DNA was partially digested with Sau3A and fractionated on a sucrose gradient. Fragments between 15 and 23 kb were ligated into EMBL3 [Stratagene, La Jolla, Calif. (USA)], packaged, plated and screened.

For example, to make the M01094 library, 200 µg of genomic DNA was partially digested with Sau3A and fractionated by size on a sucrose gradient. Fragments between 17 and 20 kb were ligated into EMBL3. Recombinant phage were packaged, plated, and screened at the time of primary plating using standard protocols. Filters were washed to a final stringency of 65° C. in 0.2×SSC and 0.2% SDS. Positive phage were isolated free of contaminating phage after two additional rounds of plating.

Clones with a prefix 514- were derived from a human genomic library made from a bone marrow sample. That sample contained 80% normal cells and 20% cells from a clonal malignancy without any evidence of a chromosome 11 abnormality. The prefix G- denotes clones obtained from a normal human male granulocyte library. The cosmid clone cos7 was isolated from a human placental DNA library [Stratagene; La Jolla, Calif. (USA)].

RNA isolation. Northern blots and RNase protection. Poly A+ RNA was isolated as previously described [Meeker et al., *Mol Cell Biol.*, 10: 1680 (1990)]. RNA was electrophoresed through formaldehyde agarose gels, and Northern blots were performed using published methods [Meeker et al. (1990), id.]. RNA markers were obtained from Bethesda Research Laboratories [BRL; Bethesda, Md. (USA)]. As a control, Northern blots were probed with the BqlI-PstI pHcGAPNR fragment from the glyceraldehyde-3-phosphate dehydrogenase (GAPDH) cDNA [Tso et al., *Nucleic Acids Res.*, 13: 2485 (1985]. Single-stranded probes for Northern blotting and protection experiments were generated using the Bluescript plasmid (Stratagene) with T3 or T7 RNA polymerase [Melton et al., *Nucleic Acids Res.*, 7: 1175 (1984)].

For RNase protection experiments [Zinn et al., *Cell*. 34: 865 (1983)], 10 μg total RNA (or 0.3 μg poly A+ RNA with 10 μg yeast tRNA) were mixed with the probe in 30 ul of hybridization buffer (80% formamide, 40 mM PIPES, pH 6.4, 400 mM NaCl, and 1 mM EDTA). Samples were heated to 85° C. for 5 minutes and then incubated at 55° C. for 12 hours. Samples were diluted with 350 ul of RNase digestion mix (10 mM Tris-HCl, pH 7.5, 300 mM NaCl, 5 mM EDTA, 40 ug/ml RNase A and 2 μg/ml RNase Ti) and incubated at 37° C. for one hour. Proteinase K (to 125 ug/ml) and SDS (to 0.5%) were added. After 15 minutes at 37° C., samples were phenol-chloroform extracted, ethanol precipitated and separated on a 6% denaturing acrylamide gel.

cDNA libraries. Five libraries from 3 cell lines were made using lambda gt1o [Huynh et al., "Construction and screening cDNA libraries in lambda gt10 and lambda gt11," pp. 49–78, IN: *DNA cloning techniques: a practical approach*, ed. D. Glover (IRL Press; Oxford) (1985)]. For M01094, one library was made with oligo-dT and random hexamer priming using established technology (Clontech), and one library was made using only oligo-dT priming of first strand synthesis and RNaseH to assist second strand synthesis (Stratagene) [Huynh et al., id.]. Two similar libraries were made for MO2058. The A253 library was made using oligo-dt priming by the method of Gubler and Hoffman, *Gene*, 25: 263–269 (1983) (Stratagene). cDNA libraries were screened with the B4.0 (FIGS. 1 and 4), EH420 (FIG. 3) and GE370 (FIGS. 3 and 4) probes.

Sequencing and computer searches. Sequencing was performed using the chain termination approach with M13 and plasmid vectors [Kraft et al., *Biotechniques*. 6: 544 (1988); and Yanisch-Peron et al., *Gene*, 33: 103 (1985)]. All sequences represent data obtained from both directions.

Protein database searches were performed using FASTA software (v.1.4d, Feb. 1991) obtained as a generous gift from W. Pearson [Johns Hopkins University; Baltimore, Md. (USA); Pearson and Lipman, *PNAS* (USA), 85: 2444 (1988)]. The parameters for searching were: ktup=2, scoring matrix=PAM250. In a search of the NBRF PIR Protein Sequence Database, 30,087 sequences were searched against the predicted 295 amino acid protein from A253. The mean initn score was 25.0 with a standard deviation of 7.21, and the mean initl score was 24.7 with a standard deviation of 6.49. Twelve scores with initn and opt greater than 100 were obtained, and all were cyclins. In the search of a different database, performed by Glenn Hammonds [Department of Medicine, UCSF (USA)], 47,645 sequences were searched, and the same result was obtained.

Densitometry. Scanning densitometry was performed using a Bio-Rad model 620 video densitometer [Hercules, Calif. (USA)]. Lanes from autoradiograms were scanned, generating a curve that related absorbance to position. The area under this curve in the region of the band was determined. Background absorbance was subtracted. Statistical analyses (least-squares fit and Wilcoxon rank sum test) were perfomed using the StatView 514+program from Brainpower, Inc. [Calabasas, Calif. (USA)].

The following examples are for purposes of illustration only and are not meant to limit the invention in any way.

EXAMPLE 1

Expression of the Bcl-1 Gene in Leukemic Cells

This example indicates by Northern blotting that expression of the bcl-1 gene is associated with the t(11;14) (q13;q32) translocation. Four cell lines derived from patients with CLL were studied. In cell lines M02058 and M01094, both having the t(11;14)(q13;q32) translocation distinct transcripts were identified. No transcripts were evident in two CLL cell lines without the translocation.

The Northern blotting was performed as indicated above wherein 5 μg of poly(A)$^+$ RNA from each of the cell lines in each lane (lanes: 1, M01129; 2, M01079; 3, M01094; and 4, M02058) was probed with the B4.0 probe. The bands for M01094 (lane 3) and M02058 (lane 4) were estimated to be 1.5 and 2.5 kb, respectively, from comparison with RNA markers. No bands were seen for M01129 (lane 1) and M01079 (lane 2). Rehybridization of the filter with a probe from the glyceraldehyde-3-phosphate dehydrogenase gene documented equal loading in the lanes.

The presence of a transcript only in the CLL lines containing the translocation evidenced tht the bcl-1 gene had been identified.

EXAMPLE 2

RNase Protection Assays

To identify the major site of bcl-1 transcription initiation, an RNase protection assay was performed as described above. RNA samples were incubated with a nucleotide antisense genomic probe (as shown in FIG. 5) extending from the NcoI site (location of translation initiation as shown in FIG. 3) and then digested with RNases A and T$_1$. The 476 bp antisense genomic probe shown in FIG. 5 could have been used in this Example and is a preferred probe for the RNase protection assays of this invention. A longer probe that extends from the NcoI site may have been used, for example, a 700 nucleotide antisense genomic probe as described in Withers et al., *Mol. Cell. Biol.*, 11 (10): 4846 (Oct. 1991).

In RNA samples from M02058, M01094, A253 and A431, a major protected fragment of 160 nucleotides was detected. In samples from M02058 and M01094, minor protected fragments could be seen migrating at about 172 and 195 bases. In samples from K562, no protected fragment could be detected. Yeast tRNA served as a negative control.

Thus, it was concluded that when such a probe extending from the NcoI site is used in an RNase protection assay according to this invention, the presence of a protected fragment in a size range of approximately 160 nucleotides is indicative of the presence of a t(11;14)(q13;q32) translocation.

EXAMPLE 3

Southern Blotting to Assess Evolutionary Conservation

Two Sourthern blot analyses were performed to assess the amount of nucleotide conservation during evolution. On one blot—Blot A—genomic DNA was from the following mammals: human, mouse, rat, pig and cow; whereas on the other blot—Blot B—was genomic DNA from nonmammalian species—fruit fly (*Drosophila melanogaster*), African clawed frog (*Xenopus laevis*), Atlantic surf claim (*Spisula solidissima*) and *S. cerevisiae*.

Ten µg of genomic DNA from each species were loaded in each lane. Both blots were hybridized with a M02058 cDNA clone. Blot A was washed to a final stringency of 1×SSC plus 0.1% SDS at 65° C. Blot B was washed to 1×SSC plus 0.1% SDS at 55° C. These experiments document that mouse, rat, pig and cow have a highly conserved bcl-1 gene (estimated at greater than 90% nucleotide homology). In Drosophila there appears to be a low level signal, whereas in Xenopus and *S. cerevisiae* there is no detectable signal.

Thus, contrasting the results from this Example with those of Example 1, indicates that unless a t(11;14)(q13;q32) is present in cells derived from bone marrow cells, that bcl-1 mRNA is at undetectable levels.

EXAMPLE 4

Selective Expression of Bcl-1 in Human Cell Lines

Northern blotting of polyA$^+$ RNA (5 µg in each lane) from the following cell lines was performed: K562; U-937; Reh; Jurkat; GM607; Tera-2; A431; and FaDu. Each lane was probed for bcl-1 expression with an M02058 cDNA clone. The major transcript at 4.4 kb was detected in three of the cell lines—Tera-2, A431 and FaDu. However, bcl-1 mRNA was not detected in any of the myeloid or lymphoid cell lines—K562, U-937, Reh, Jurkat and GM607.

Thus, contrasting the results from this Example with those of Example 1, indicates that unless a t(11;14)(q13;q32) is present in cells derived from bone marrow cells, that bcl-1 mRNA is at undetectable levels.

EXAMPLE 5

PCR

PCR was used to clone the M02058 translocation. Primers (A) and (B) described above under PCR Assays were used. An 85 bp fragment could be amplified from M02058 DNA [containing t(11;14)(q13q32)] but not from control samples.

Amplification of genomic DNA was carried out using published methods [Saiki et al., supra]. Genomic DNA (50–250 ng) was amplified in 100 µl containing 10 mM Tris-HCl$_1$, pH 8.3, 50 mM KCl, 1.5 mM MgCl$_2$, 0.01% (weight/volume) gelatin, 0.2 mM each dNTP and 2.5 U Taq polymerase [Perkin-Elmer/Cetus, Norwalk, Conn. (USA)]. Reactions were performed in an automated thermal cycler with denaturation at 95° C. for 1 minute annealing at 45–50° C. for 1 minute and extension at 72° C. for 3 minutes.

For subcloning, the polymerase chain reaction (PCR) products were separated on agarose gels. The specific product was isolated from a gel slice. The fragment was kinased, ligated into a pUC18 and transformed into competent *E. coli* strain Dh5aF' [Bethesda Research Laboratories, Bethesda, Md. (USA)].

The 85 bp fragment was cloned and sequenced. It falls within a 7 bp stretch on chromosome 11 in which two other cloned breakpoints occur [those for CLL 1386 and CLL 271 described in Tsujimoto et al., *Nature*, 315: 340 (1986) and Tsujimoto et al., *Science*, 224: 1403 (1984)].

EXAMPLE 6

Amplification of bcl-1 Locus in Human Tumor Cell Lines and Expression

Amplification of bcl-1 in cell line DNA was assessed by Southern blot hybridization using the pB4.0 probe (FIGS. 1 and 4). Amplification was quantitated by scanning densitometry of autoradiograms. In order to normalize for DNA loading, blots were stripped and subsequently rehybridized with a probe for the human insulin gene—phins214 [a 1.6 kb human insulin gene probe obtained from the ATCC, Bell et al., *Diabetes*, 33: 176 (1984)]. Because the insulin gene resides on the short arm of chromosome 11 (11p), the number of copies of the bcl-1 gene is normalized for extra copies of chromosome 11. Therefore, the approach detected only amplification, not aneuploidy.

Amplifications of DNA sequences at the bcl-1 locus at 11q13 have been reported in numerous human tumors, both primary tumors and tumor cell lines. The data from the instant experiments [Faust and Meeker, *Cancer Res.*, 52: 2460 (May 1, 1992)] show that 10 of 22 human cell lines examined contained amplification of sequences within the region of the bcl-1 gene.

Amplification of bcl-1 was found in the following cell lines:

A431 (epidermoid carcinoma);
FaDU and Detroit 562 (pharyngeal carcinomas);
BT474; MDA-MB-134; T47D and MDA-MB-361 (breast carcinomas);
A253 (submaxillary carcinoma);
T98G (glioblastoma); and
HOS (osteosarcoma).

By Northern blot analysis of mRNA, it was shown that a large fraction of breast carcinomas express high levels of bcl-1 [Faust and Meeker, supra]. Generally, breast adenocarcinoma cell lines and squamous cell carcinoma cell lines from a variety of organs (cervix, head and neck, submaxillary gland, and vulva) express higher levels of bcl-1 than other solid tumors (glioblastomas, osteosarcomas, renal and gastric carcinomas). A cell line derived from normal breast cells (HBL-100) also exhibited detectable levels of bcl-1 mRNA.

The data of this example supports the hypothesis that amplification leads to increased levels of bcl-1 mRNA. Bcl-1 is apparently the gene from 11q13, rather than hst-1 or int-1, that results in deregulated cell growth when 11q13 is amplified [Faust and Meeker supra].

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated. It is intended that the scope of the invention be defined by the claims appended hereto.

All references cited herein are hereby incorporated by reference.

What is claimed is:

1. A method of detecting the presence of an abnormality of the bcl-1 locus on chromosome 11 in tumor cells, the method comprising:

contacting nucleic acids from the tumor cells with a nucleic acid probe that comprises isolated and purified polynucleotide sequences that are substantially complementary to and specifically hybridize under stringent conditions (i) to SEQ ID NO: 7 and (ii) to nucleic acid sequences of the MO20508 translocation breakpoint to form a hybridization complex; and detecting the hybridization complex;

thereby detecting the presence of the abnormality of the bcl-1 locus on chromosome 11 in the tumor cells.

2. The method of claim 1, wherein the polynucleotide sequences are also substantially complementary to and hybridize under stringent conditions to all or a portion of one or more introns of the bcl-1 gene.

3. The method of claim 1, wherein the polynucleotide sequences are labeled.

4. The method of claim 3, wherein the label is a fluorescent label.

5. The method of claim 3, wherein the abnormality is an amplification of the bcl-1 gene.

6. The method of claim 5, wherein the amplification is detected by detecting the extent and brightness of signal from the labeled polynucleotide sequences.

7. The method of claim 1, wherein the step of contacting is carried out by using in situ hybridization techniques.

8. The method of claim 7, wherein the polynucleotide sequences are labeled with a fluorescent label.

* * * * *

SEQUENCE LISTING

```
(1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

AATAATCAAC TC                                                                12

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:2:

GTCACCGTCT CCTCAGGT                                                          18

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:3:

GAGCTCCCTG AACACCTGGC                                                        20

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: PCR primer (iii) HYPOTHETICAL: NO (iv) ANTI-SENSE: NO (xi) SEQUENCE DESCRIPTION: SEQ ID NO:4:

CTCATACGGT GTGTAGC                                                17

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:5:

GGTTAGACTG TGATTAGC                                               18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:6:

ACCTGAGGAG ACGGTGAC                                               18

(2) INFORMATION FOR SEQ ID NO:7:

(i) SEQUENCE CHARACTERISTICS:
        (A) LENGTH: 4221 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 142..1026

(xi) SEQUENCE DESCRIPTION: SEQ ID NO:7:

```
GTAGCAGCGA GCAGCAGAGT CCGCACGCTC CGGCGAGGGG CAGAAGAGCG CGAGGGAGCG    60

CGGGGCAGCA GAAGCGAGAG CCGAGCGCGG ACCCAGCCAG GACCCACAGC CCTCCCCAGC   120

TGCCCAGGAA GAGCCCCAGC C ATG GAA CAC CAG CTC CTG TGC TGC GAA GTG    171
                         Met Glu His Gln Leu Leu Cys Cys Glu Val
                          1               5                  10

GAA ACC ATC CGC CGC GCG TAC CCC GAT GCC AAC CTC CTC AAC GAC CGG    219
Glu Thr Ile Arg Arg Ala Tyr Pro Asp Ala Asn Leu Leu Asn Asp Arg
             15                  20                  25
```

```
GTG CTG CGG GCC ATG CTG AAG GCG GAG GAG ACC TGC GCG CCC TCG GTG      267
Val Leu Arg Ala Met Leu Lys Ala Glu Glu Thr Cys Ala Pro Ser Val
             30                  35                  40

TCC TAC TTC AAA TGT GTG CAG AAG GAG GTC CTG CCG TCC ATG CGG AAG      315
Ser Tyr Phe Lys Cys Val Gln Lys Glu Val Leu Pro Ser Met Arg Lys
             45                  50                  55

ATC GTC GCC ACC TGG ATG CTG GAG GTC TGC GAG GAA CAG AAG TGC GAG      363
Ile Val Ala Thr Trp Met Leu Glu Val Cys Glu Glu Gln Lys Cys Glu
 60                  65                  70

GAG GAG GTC TTC CCG CTG GCC ATG AAC TAC CTG GAC CGC TTC CTG TCG      411
Glu Glu Val Phe Pro Leu Ala Met Asn Tyr Leu Asp Arg Phe Leu Ser
 75                  80                  85                  90

CTG GAG CCC GTG AAA AAG AGC CGC CTG CAG CTG CTG GGG GCC ACT TGC      459
Leu Glu Pro Val Lys Lys Ser Arg Leu Gln Leu Leu Gly Ala Thr Cys
             95                 100                 105

ATG TTC GTG GCC TCT AAG ATG AAG GAG ACC ATC CCC CTG ACG GCC GAG      507
Met Phe Val Ala Ser Lys Met Lys Glu Thr Ile Pro Leu Thr Ala Glu
            110                 115                 120

AAG CTG TGC ATC TAC ACC GAC AAC TCC ATC CGG CCC GAG GAG CTG CTG      555
Lys Leu Cys Ile Tyr Thr Asp Asn Ser Ile Arg Pro Glu Glu Leu Leu
            125                 130                 135

CAA ATG GAG CTG CTC CTG GTG AAC AAG CTC AAG TGG AAC CTG GCC GCA      603
Gln Met Glu Leu Leu Leu Val Asn Lys Leu Lys Trp Asn Leu Ala Ala
140                 145                 150

ATG ACC CCG CAC GAT TTC ATT GAA CAC TTC CTC TCC AAA ATG CCA GAG      651
Met Thr Pro His Asp Phe Ile Glu His Phe Leu Ser Lys Met Pro Glu
155                 160                 165                 170

GCG GAG GAG AAC AAA CAG ATC ATC CGC AAA CAC GCG CAG ACC TTC GTT      699
Ala Glu Glu Asn Lys Gln Ile Ile Arg Lys His Ala Gln Thr Phe Val
            175                 180                 185

GCC CTC TGT GCC ACA GAT GTG AAG TTC ATT TCC AAT CCG CCC TCC ATG      747
Ala Leu Cys Ala Thr Asp Val Lys Phe Ile Ser Asn Pro Pro Ser Met
            190                 195                 200

GTG GCA GCG GGG AGC GTG GTG GCC GCA GTG CAA GGC CTG AAC CTG AGG      795
Val Ala Ala Gly Ser Val Val Ala Ala Val Gln Gly Leu Asn Leu Arg
            205                 210                 215

AGC CCC AAC AAC TTC CTG TCC TAC TAC CGC CTC ACA CGC TTC CTC TCC      843
Ser Pro Asn Asn Phe Leu Ser Tyr Tyr Arg Leu Thr Arg Phe Leu Ser
220                 225                 230

AGA GTG ATC AAG TGT GAC CCG GAC TGC CTC CGG GCC TGC CAG GAG CAG      891
Arg Val Ile Lys Cys Asp Pro Asp Cys Leu Arg Ala Cys Gln Glu Gln
235                 240                 245                 250

ATC GAA GCC CTG CTG GAG TCA AGC CTG CGC CAG GCC CAG CAG AAC ATG      939
Ile Glu Ala Leu Leu Glu Ser Ser Leu Arg Gln Ala Gln Gln Asn Met
            255                 260                 265

GAC CCC AAG GCC GCC GAG GAG GAG GAA GAG GAG GAG GAG GAG GTG GAC      987
Asp Pro Lys Ala Ala Glu Glu Glu Glu Glu Glu Glu Glu Glu Val Asp
            270                 275                 280

CTG GCT TGC ACA CCC ACC GAC GTG CGG GAC GTG GAC ATC TGAGGGCGCC      1036
Leu Ala Cys Thr Pro Thr Asp Val Arg Asp Val Asp Ile
            285                 290                 295

AGGCAGGCGG GCGCCACCGC CACCCGCAGC GAGGGCGGAG CCGGCCCCAG GTGCTCCACT    1096

GACAGTCCCT CCTCTCCGGA GCATTTTGAT ACCAGAAGGG AAAGCTTCAT TCTCCTTGTT    1156

GTTGGTTGTT TTTTCCTTTG CTCTTTCCCC CTTCCATCTC TGACTTAAGC AAAAGAAAAA    1216

GATTACCCAA AAACTGTCTT TAAAAGAGAG AGAGAGAAAA AAAAAATAGT ATTTGCATAA    1276

CCCTGAGCGG TGGGGGAGGA GGGTTGTGCT ACAGATGATA GAGGATTTTA TACCCCAATA    1336

ATCAACTCGT TTTTATATTA ATGTACTTGT TTCTCTGTTG TAAGAATAGG CATTAACACA    1396
```

-continued

```
AAGGAGGCGT CTCGGGAGAG GATTAGGTTC CATCCTTTAC GTGTTTAAAA AAAAGCATAA    1456

AAACATTTTA AAAACATAGA AAAATTCAGC AAACCATTTT TAAAGTAGAA GAGGGTTTTA    1516

GGTAGAAAAA CATATTCTTG TGCTTTTCCT GATAAAGCAC AGCTGTAGTG GGGTTCTAGG    1576

CATCTCTGTA CTTTGCTTGC TCATATGCAT GTAGTCACTT TATAAGTCAT TGTATGTTAT    1636

TATATTCCGT AGGTAGATGT GTAACCTCTT CACCTTATTC ATGGCTGAAG TCACCTCTTG    1696

GTTACAGTAG CGTAGCGTGG CCGTGTGCAT GTCCTTTGCG CCTGTGACCA CCACCCCAAC    1756

AAACCATCCA GTGACAAACC ATCCAGTGGA GGTTTGTCGG GCACCAGCCA GCGTAGCAGG    1816

GTCGGGAAAG GCCACCTGTC CCACTCCTAC GATACGCTAC TATAAAGAGA AGACGAAATA    1876

GTGACATAAT ATATTCTATT TTTATACTCT TCCTATTTTT GTAGTGACCT GTTTATGAGA    1936

TGCTGGTTTT CTACCCAACG GCCCTGCAGC CAGCTCACGT CCAGGTTCAA CCCACAGCTA    1996

CTTGGTTTGT GTTCTTCTTC ATATTCTAAA ACCATTCCAT TTCCAAGCAC TTTCAGTCCA    2056

ATAGGTGTAG GAAATAGCGC TGTTTTTGTT GTGTGTGCAG GGAGGGCAGT TTTCTAATGG    2116

AATGGTTTGG GAATATCCAT GTACTTGTTT GCAAGCAGGA CTTTGAGGCA AGTGTGGGCC    2176

ACTGTGGTGG CAGTGGAGGT GGGGTGTTTG GGAGGCTGCG TGCCAGTCAA GAAGAAAAAG    2236

GTTTGCATTC TCACATTGCC AGGATGATAA GTTCCTTTCC TTTTCTTTAA AGAAGTTGAA    2296

GTTTAGGAAT CCTTTGGTGC CAACTGGTGT TTGAAAGTAG GGACCTCAGA GGTTTACCTA    2356

GAGAACAGGT GGTTTTTAAG GGTTATCTTA GATGTTCAC ACCGGAAGGT TTTTAAACAC    2416

TAAAATATAT AATTTATAGT TAAGGCTAAA AAGTATATTT ATTGCAGAGG ATGTTCATAA    2476

GGCCAGTATG ATTTATAAAT GCAATCTCCC CTTGATTTAA ACACACAGAT ACACACACAC    2536

ACACACACAC ACACACAAAC CTTCTGCCTT TGATGTTACA GATTTAATAC AGTTTATTTT    2596

TAAAGATAGA TCCTTTTATA GGTGAGAAAA AAACAATCTG GAAGAAAAAA ACCACACAAA    2656

GACATTGATT CAGCCTGTTT GGCGTTTCCC AGAGTCATCT GATTGGACAG GCATGGGTGC    2716

AAGGAAAATT AGGGTACTCA ACCTAAGTTC GGTTCCGATG AATTCTTATC CCCTGCCCCT    2776

TCCTTTAAAA AACTTAGTGA CAAAATAGAC AATTTGCACA TCTTGGCTAT GTAATTCTTG    2836

TAATTTTTAT TTAGGAAGTG TTGAAGGGAG GTGGCAAGAG TGTGGAGGCT GACGTGTGAG    2896

GGAGGACAGG CGGGAGGAGG TGTGAGGAGG AGGCTCCCGA GGGGAAGGGG CGGTGCCCAC    2956

ACCGGGGACA GGCCGCAGCT CCATTTTCTT ATTGCGCTGC TACCGTTGAC TTCCAGGCAC    3016

GGTTTGGAAA TATTCACATC GCTTCTGTGT ATCTCTTTCA CATTGTTTGC TGCTATTGGA    3076

GGATCAGTTT TTTGTTTTAC AATGTCATAT ACTGCCATGT ACTAGTTTTA GTTTTCTCTT    3136

AGAACATTGT ATTACAGATG CCTTTTTTGT AGTTTTTTTT TTTTTTTAT GTGATCAATT    3196

TTGACTTAAT GTGATTACTG CTCTATTCCA AAAAGGTTGC TGTTTCACAA TACCTCATGC    3256

TTCACTTAGC CATGGTGGAC CCAGCGGGCA GGTTCTGCCT GCTTTGGCGG GCAGACACGC    3316

GGGCGCGATC CCACACAGGC TGGCGGGGGC CGGCCCCGAG GCCGCGTGCG TGAGAACCGC    3376

GCCGGTGTCC CCAGAGACCA GGCTGTGTCC CTCTTCTCTT CCCTGCGCCT GTGATGCTGG    3436

GCACTTCATC TGATCGGGGG CGTAGCATCA TAGTAGTTTT TACAGCTGTG TTATTCTTTG    3496

CGTGTAGCTA TGGAAGTTGC ATAATTATTA TTATTATTAT TATAACAAGT GTGTCTTACG    3556

TGCCACCACG GCGTTGTACC TGTAGGACTC TCATTCGGGA TGATTGGAAT AGCTTCTGGA    3616

ATTTGTTCAA GTTTTGGGTA TGTTTAATCT GTTATGTACT AGTGTTCTGT TTGTTATTGT    3676

TTTGTTAATT ACACCATAAT GCTAATTTAA AGAGACTCCA AATCTCAATG AAGCCAGCTC    3736
```

```
ACAGTGCTGT GTGCCCCGGT CATCTAGCAA GCTGCCGAAC CAAAAGAATT TGCACCCCGC    3796

TGCGGGCCCA CGTGGTTGGG GCCCTGCCCT GGCAGGGTCA TCCTGTGCTC GGAGGCCATC    3856

TCGGGCACAG GCCCACCCCG CCCCACCCCT CCAGAACACG GCTCACGCTT ACCTCAACCA    3916

TCCTGGCTGC GGCGTCTGTC TGAACCACGC GGGGGCCTTG AGGGACGCTT TGTCTGTCGT    3976

GATGGGGCAA GGGCACAAGT CCTGGATGTT GTGTGTATCG AGAGGCCAAA GGCTGGTGGC    4036

AAGTGCACGG GGCACAGCGG AGTCTGTCCT GTGACGCGCA AGTCTGAGGG TCTGGGCGGC    4096

GGGCGGCTGG GTCTGTGCAT TTCTGGTTGC ACCGCGGCGC TTCCCAGCAC CAACATGTAA    4156

CCGGCATGTT TCCAGCAGAA GACAAAAAGA CAAACATGAA AGTCTAGAAA TAAAACTGGT    4216

AAAAC                                                                4221
```

(2) INFORMATION FOR SEQ ID NO:8:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:8:

```
Met Glu His Gln Leu Leu Cys Cys Glu Val Glu Thr Ile Arg Arg Ala
 1               5                  10                  15

Tyr Pro Asp Ala Asn Leu Leu Asn Asp Arg Val Leu Arg Ala Met Leu
                20                  25                  30

Lys Ala Glu Glu Thr Cys Ala Pro Ser Val Ser Tyr Phe Lys Cys Val
            35                  40                  45

Gln Lys Glu Val Leu Pro Ser Met Arg Lys Ile Val Ala Thr Trp Met
        50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
```

```
                  260                 265                 270
Glu Glu Glu Glu Glu Glu Glu Glu Val Asp Leu Ala Cys Thr Pro Thr
        275                 280                 285

Asp Val Arg Asp Val Asp Ile
        290                 295
```

(2) INFORMATION FOR SEQ ID NO:9:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:9:

```
CTCGAGGCGG ACGGGCCCCC CTGCACCCCT CTTCCCTGGC GGGGAGAAAG GCTGCAGCGG    60
GGCGATTTGC ATTTCTATGA AAACCGGACT ACAGGGGCAA CTCCGCCGCA GGGCAGGCGC   120
GGCGCCTCAG GGATGGCTTT TGGGCTCTGC CCTCGCTGCT CCCGGCGTTT GGCGCCCGCG   180
CCCCCTCCCC CTGCGCCCGC CCCCGCCCCC CTCCCGCTCC CATTCTCTGC CGGGCTTTGA   240
TCTTTGCTTA ACAACAGTAA CGTCACACGG ACTACAGGGG AGTTTTGTTG AAGTTGCAAA   300
GTCCTGGAGC CTCCAGAGGG CTGTCGGCGC AGTAGCAGCG AGCAGCAGAG TCCGCACGCT   360
CCGGCGAGGG GCAGAAGAGC GCGAGGGAGC GCGGGGCAGC AGAAGCGAGA GCCGAGCGCG   420
GACCCAGCCA GGACCCACAG CCCTCCCCAG CTGCCCAGGA AGAGCCCCAG CCATGG       476
```

(2) INFORMATION FOR SEQ ID NO:10:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
AATTCTGGGG ACACAATTGG GCCCGTCACA CATGGGGTGG GCTCCAAGGG AAGTTGGTGC    60
AGTGGTCCTA GCTCTTGTGA CCGCATAAGC TCCAAAGGCT TGTTGGTATT CAGACCTGAG   120
GAATCAGAGG CCCAAGGAGG ACAGGAGACA CGGCTTTAGG TCCCCAGTTC TTTGTGGCAG   180
GACTGCCTCT CACCCAGGTC TCCACTCCCA GGAGACCTGT GGAAGGAGAA GACCCCTTCC   240
ACACTTGATG CCAGGCTTCT TATTACACAG ACCCTACTGC CTCAAAGGCC TCAAGTGACC   300
CCGGACTCAC TCACGCCCTG CAAGCAGGGG AACTGTCAGC ATCTGGCTAG GCCATGTCA    360
GCTGCGATGG GCTGGGGCGA GCTACAGTAA GAGTGGGGCC CGTGGAGTGG GTTCCTGGGG   420
GAGCCCATCG TATGTCTAGC AGTTGCGGGC TTTTTGGGAT GTCAACCACC TCTGCTGGGA   480
AGGTGCTGGG CGTGGGTGGG TGGGTAAGAT GCTGGCTGAG TCATCTGTGT CCCCGAAATA   540
GGCTGTGGAA TGGGGAAGCT                                              560
```